United States Patent
Borchert et al.

(10) Patent No.: US 6,831,182 B2
(45) Date of Patent: Dec. 14, 2004

(54) METHOD FOR THE HYDROGENATION OF MALEIC ANHYDRIDE AND RELATED COMPOUNDS IN TWO SERIAL REACTION ZONES

(75) Inventors: Holger Borchert, Offstein (DE); Stephan Schlitter, Limburgerhof (DE); Rolf-Hartmuth Fischer, Heidelberg (DE); Markus Rösch, Oppenheim (DE); Frank Stein, Bad Dürkheim (DE); Ralf-Thomas Rahn, Mannheim (DE); Alexander Weck, Freinsheim (DE); Gerd Kaibel, Lampertheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/433,424

(22) PCT Filed: Dec. 7, 2001

(86) PCT No.: PCT/EP01/14393

§ 371 (c)(1),
(2), (4) Date: Jun. 4, 2003

(87) PCT Pub. No.: WO02/48129

PCT Pub. Date: Jun. 20, 2002

(65) Prior Publication Data

US 2004/0034240 A1 Feb. 19, 2004

(30) Foreign Application Priority Data

Dec. 11, 2000 (DE) .......................................... 100 61 557

(51) Int. Cl.$^7$ ..................... C07D 307/08; C07D 307/32
(52) U.S. Cl. ..................... 549/508; 549/325; 549/326; 549/429
(58) Field of Search ................................ 549/508, 325, 549/326, 429

(56) References Cited

U.S. PATENT DOCUMENTS

| | | | |
|---|---|---|---|
| 3,065,243 A | 11/1962 | Dunlop et al. | 260/343 |
| 3,580,930 A | 5/1971 | Miya et al. | 260/343 |
| 4,006,165 A | 2/1977 | Michalczyk et al. | 260/343 |
| 5,072,009 A | 12/1991 | Budge et al. | 549/508 |
| 5,122,495 A | 6/1992 | Taylor et al. | 502/183 |
| 5,149,836 A | 9/1992 | DeThomas et al. | 549/325 |
| 5,536,845 A | 7/1996 | Berthe et al. | 549/79 |
| 6,008,375 A | 12/1999 | Bergfeld et al. | 548/554 |

FOREIGN PATENT DOCUMENTS

| | | |
|---|---|---|
| EP | 404408 | 12/1990 |
| EP | 638565 | 2/1995 |
| JP | 2-233631 | 9/1990 |
| WO | 95/22539 | 8/1995 |
| WO | 97/24346 | 7/1997 |
| WO | 99/35136 | 7/1999 |
| WO | 99/35139 | 7/1999 |
| WO | 99/38856 | 8/1999 |

*Primary Examiner*—Ba K. Trinh
(74) *Attorney, Agent, or Firm*—Keil & Weinkauf

(57) ABSTRACT

The present invention relates to a process for the gas-phase hydrogenation of $C_4$-dicarboxylic acids and/or their derivatives over a catalyst based on copper oxide to give substituted or unsubstituted γ-butyrolactone and/or tetrahydrofuran, which comprises, which a first reaction zone in which the $C_4$-dicarboxylic acid and/or its derivatives is/are reacted to give a mixture comprising a substituted or unsubstituted γ-butyrolactone as main product and a subsequent second reaction zone in which the substituted or unsubstituted γ-butyrolactone present in the mixture from the first hydrogenation step is reacted at a temperature lower than the temperature in the first hydrogenation step to give substituted or unsubstituted tetrahydrofuran.

18 Claims, No Drawings

METHOD FOR THE HYDROGENATION OF MALEIC ANHYDRIDE AND RELATED COMPOUNDS IN TWO SERIAL REACTION ZONES

The present invention relates to a process for preparing unsubstituted or alkyl-substituted γ-butyrolactone and tetrahydrofuran by catalytic hydrogenation in the gas phase of substrates selected from the group consisting of maleic acid and succinic acid and derivatives of these acids. For the purposes of the present invention, such derivatives are esters and anhydrides which, like the acids themselves, may bear one or more alkyl substituents. The process makes it possible to achieve high yields and the ratio of the two products can be set over a wide range. The process of the present invention is carried out in two reaction zones connected in series.

The preparation of γ-butyrolactone (GBL) and tetrahydrofuran THF) by gas-phase hydrogenation of maleic anhydride (MA) is a reaction which has been known for many years. Numerous catalyst systems for carrying out this catalytic reaction are described in the literature. These are mostly Cr-containing. Depending on the composition of the catalyst and the reaction parameters selected, such catalysts give different product distributions.

Apart from MA, further possible starting materials for preparing GBL and THF are maleic acid itself, succinic acid and its anhydride and also esters of these acids. If GBL and THF bearing alkyl substituents are to be prepared, the appropriately alkyl-substituted derivatives of the abovementioned acids, esters and anhydrides can be used.

U.S. Pat. No. 3,065,243 discloses a process in which copper chromite is used as catalyst. According to the description and examples, this process forms considerable amounts of succinic anhydride (SA) which has to be circulated. As is well known, this frequently results in process engineering problems due to crystallization of SA or succinic acid formed therefrom followed by blockage of pipes.

Further copper chromite catalysts for the hydrogenation of MA are disclosed, for example, in the publications U.S. Pat. Nos. 3,580,930, 4,006,165, EP-A 638 565 and WO 99/38856. According to these disclosures, high yields of GBL can be achieved using the catalysts described there. THF is in each case formed only in traces. However, larger amounts of THF are often desired for a number of reasons.

A process which allows this is disclosed in U.S. Pat. No. 5,072,009. The catalysts used according to this patent have the formula $Cu_1Zn_bAl_cM_dO_x$, where M is at least one element selected from the group consisting of the elements of groups IIA and IIIA, VA, VIII, Ag, Au, groups IIIB to VIIB and the lanthanides and actinides of the Periodic Table of the Elements, b is from 0.001 to 500, c is from 0.001 to 500 and d is from 0 to <200 and x corresponds to the number of oxygen atoms required according to the valence criteria. Although it is stated that it is not necessary for chromium to be present in the catalysts disclosed in this patent, all examples describe chromium-containing catalysts. According to these examples, the maximum THF yield is 96%, and the hydrogenation is carried out at pressures of from 20 to 40 bar.

An in-principle disadvantage of all the above-described catalyst systems is the presence of chromium oxide whose use should be avoided because of the high toxicity. Cr-free catalyst systems for preparing GBL by hydrogenation of MA have also been described in the prior art. Examples of such catalyst systems may be found in the publications WO 99/35139 (Cu—Zn oxide), WO 95/22539 (Cu—Zn—Zr) and U.S. Pat. No. 5,122,495 (Cu—Zn—Al oxide). All these catalyst systems make it possible to achieve high yields of GBL, up to 98%, but the formation of THF is not observed or only traces are formed. Although the formation of THF can, as is known, be promoted by increasing the reaction temperature or having a longer residence time in the reactor, this at the same time also increases the proportion of undesirable by-products, for example butanol, butane, ethanol or ethane.

A catalyst made up exclusively of copper and aluminum oxides for the gas-phase hydrogenation of MA to GBL is disclosed in WO 97/24346. Here too, the same disadvantages as in the publications described in the previous paragraph, namely formation of THF in only minor amounts or traces, are encountered.

The use of a catalyst having essentially the same composition as described in WO 97/24346, namely based on Cu—Al oxides, is also disclosed in JP 2 233 631. The object of that invention is to carry out the hydrogenation of MA in such a way that THF and 1,4-butanediol are formed as main products and only small amounts, if any, of GBL are formed. This is achieved by the use of the catalysts based on mixed Cu—Al oxides and by adhering to particular reaction conditions. Typical mixtures obtained by means of this process comprise from about 15 to 20 mol % of 1,4-butanediol and from 60 to 80 mol % of THF, with the amount of THF even being able to be increased to over 99 mol % according to one example. This is achieved by using GBL as solvent in a large excess. If, on the other hand, no solvent is employed, the yields drop significantly to values of 75%.

In contrast, EP-A 0 404 408 discloses a catalyst for the hydrogenation of MA whose structure is different in principle from that of the catalysts in the above-mentioned references. Here, the catalytically active material corresponds essentially to the material disclosed in the above-cited U.S. Pat. No. 5,072,009. The material is then applied to an essentially inert, at least partly porous support having an external surface. The catalytically active material adheres to the outer surface of the support. In contrast to the corresponding, unsupported catalyst, which gives THF as main product, this catalyst forms GBL as preferred product. Here too, Cr is present in all catalysts used in the examples. Another disadvantage is the large amount of SA formed.

All the types of catalyst described in the abovementioned publications have the disadvantage that they still produce a large amount of undesired by-product or can be used only for the preparation of one of the main products THF and GBL which may be desired in principle. In addition, Cr is frequently present in the catalysts.

A two-stage process for the hydrogenation of MA is described in U.S. Pat. No. 5,149,836. This process enables GBL and THF to be produced in an adjustable selectivity ratio of from 15 to 92% of GBL or from 7 to 83% of THF. The process comprises a first step in which MA is hydrogenated over a first catalyst bed comprising from 30 to 65% by weight of CuO, from 18 to 50% by weight of ZnO and from 8 to 22% by weight of $Al_2O_3$ to give a gas mixture comprising predominantly GBL. The GBL obtained in the first step is hydrogenated to THF over a second catalyst bed comprising from 10 to 50% by weight of CuO, from 30 to 65% by weight of ZnO and from 3 to 20% by weight of $Cr_2O_3$. The first hydrogenation is carried out at from 200 to 400° C., while the second is carried out at from 200 to 350° C., preferably from 250 to 280° C. According to the examples, the reaction temperature in the first step is from 245 to 275° C. while that in the second step is from 250 to 280° C. At a temperature of 250° C., mainly butanediol is formed in the second hydrogenation step, while mainly THF is formed at 280° C.

WO 99/35136 describes a further process for preparing THF and GBL in variable relative amounts. Starting materials used are maleic anhydride or succinic anhydride or fumaric esters. In a first step, these are reacted with hydrogen over a copper-based heterogeneous catalyst, preferably a copper-zinc oxide or stabilized copper chromite catalyst. In a second reaction step, an acidic silicon-aluminum oxide is used. Disadvantages of this process are the use of two entirely different catalysts and also the limited flexibility in respect of the product mix, since the GBL:THF ratio can be varied only in the range from 70:30 to 40:60.

It is an object of the present invention to provide a process for the gas-phase hydrogenation of maleic acid and/or succinic acid and/or the abovementioned derivatives by means of which substituted or unsubstituted GBL and/or THF can be prepared and which allows these two products to be prepared in widely variable relative amounts and in high yields.

We have found that this object is achieved by a process for the gas-phase hydrogenation of $C_4$-dicarboxylic acids and/or their derivatives over a catalyst based on copper oxide to give substituted or unsubstituted γ-butyrolactone and/or tetrahydrofuran, which process comprises a first hydrogenation step in which the $C_4$-dicarboxylic acid or its derivative is reacted to give a mixture comprising a substituted or unsubstituted γ-butyrolactone as main product and a subsequent second hydrogenation step in which the substituted or unsubstituted γ-butyrolactone present in the mixture from the first hydrogenation step is reacted at a temperature lower than the temperature in the first hydrogenation step to give substituted or unsubstituted tetrahydrofuran.

For the purposes of the present invention the term $C_4$-dicarboxylic acids and their derivatives refers to maleic acid and succinic acid which may bear one or more $C_1$–$C_6$-alkyl substituents and also the anhydrides and esters of these unsubstituted or alkyl-substituted acids. An example of such an acid is citraconic acid. Preference is given to using MA.

It has surprisingly been found that the use of the Cr-free hydrogenation catalysts arranged in series and adherence to particular reaction conditions enable the product ratio of GBL:THF to be varied within wide limits.

In this process, a Cr-free catalyst based on copper oxide is used in both reaction zones. The copper oxide is present in amounts of from 5 to 100% by weight. The catalyst can further comprise one or more metals or compounds thereof, for example oxides, selected from the group consisting of Al, Si, Zn, La, Ce, the elements of groups IIIA to VIIIA and of groups IA and IIA in amounts of from 0 to 95% by weight. The catalysts used in the two reaction zones may be identical or can have different compositions. Which of these two embodiments is chosen depends, for example, on the desired product composition.

For the purposes of the present invention, the group of the Periodic Table of the Elements is designated in accordance with the old IUPAC nomenclature.

The catalysts used in the first hydrogenation step preferably comprise from 5 to 100% by weight of CuO, from 0 to 80% by weight of ZnO and from 0 to 95% by weight of $Al_2O_3$, in particular from 20 to 80% by weight of CuO, from 10 to 40% by weight of ZnO and from 5 to 60% by weight of $Al_2O_3$. The catalysts employed in the second hydrogenation step preferably comprise from 5 to 80% by weight of CuO, from 0 to 80% by weight of ZnO and from 0 to 60% by weight of $Al_2O_3$, in particular from 20 to 60% by weight of CuO, from 0 to 60% by weight of ZnO and from 10 to 50% by weight of $Al_2O_3$.

The respective metals may also be present in elemental form in the mixed oxide used according to the invention. These are formed, in particular, under a reducing hydrogen atmosphere. In general, the catalyst is subjected to activation, in general pretreatment with hydrogen, before use in the reaction. This produces the active catalyst species. It is generally achieved by partial reduction of the oxides present in the catalyst mixture to the elemental metal which is active in the catalytic reaction occurring in the process of the present invention.

The first hydrogenation step is preferably carried out at $\geq 200°$ C., in particular from 230 to 300° C. The primary product of this first hydrogenation is substituted or unsubstituted succinic anhydride (SA) which is then hydrogenated further to substituted or unsubstituted GBL. For this reason, deactivation of the catalyst due to coating with relative nonvolatile SA is observed when the temperature is too low, i.e. the hydrogenation is carried out at below 200° C.

The reaction is carried out so that the starting mixture is reacted with hydrogen in the first reaction zone to form a product mixture comprising predominantly substituted or unsubstituted GBL. For this purpose, the starting mixture is vaporized and passed through the reactor together with a hydrogen-containing gas stream. Here, the proportion of hydrogen in the gas stream is preferably high. It is possible for other gaseous components such as water vapor, hydrocarbons such as methane, ethane or n-butane or carbon monoxide to be present. The reaction conditions (temperature, pressure, GHSV, MA concentration at the inlet) and the catalyst are chosen so that the GBL yield is maximized while the formation of SA or overhydrogenation products occurs to a minor extent. GBL yields of at least about 30% are sought. GBL yields are preferably at least about 50%, in particular at least about 70%. Excessively high temperatures promote the formation of undesirable by-products.

The concentration of the starting material is from 0.1 to 5% by volume, preferably from 0.2 to 3% by volume. At significantly higher concentrations, the starting material condenses in the reactor and coats the catalyst with a liquid film. This is observed in particular in the case of MA. Significantly higher concentrations would reduce the space-time yield and make the process unnecessarily expensive. The GHSV (gas hourly space velocity=volume flow of the reaction gas at STP divided by the bed volume of catalyst) is set so that the starting materials and the SA are reacted completely; it is preferably set to from 100 to 10000 $h^{-1}$. The pressure is from 0.5 to 100 bar, preferably from 1 to 50 bar, in particular <20 bar. Although higher pressures aid the reaction of the starting materials, they also increase the costs of the process. Suitable reactors are tube reactors, shell-and-tube reactors in which the catalyst is present as a fixed bed and fluidized-bed reactors.

In the second reaction zone, the temperature is set to a value below that in the previous hydrogenation step. The second hydrogenation is preferably carried out at $\leq 280°$ C., preferably from 150 to 240° C. Excessively high temperatures lead to formation of by-products by overhydrogenation and thus to a reduction in the yield. The gas leaving the first reaction zone is generally passed to the second zone, preferably without further work-up. Since the temperature of the second step is lower than that of the first, the reaction gas should be cooled to the temperature of the second step. Reactors suitable for the second step are likewise tube reactors, shell-and-tube reactors or fluidized-bed reactors.

The reaction conditions (temperature, pressure, GHSV) and the catalyst in the second reaction zone are chosen so that GBL is converted into substituted or unsubstituted THF in the desired selectivity ratio. Temperatures which are too low lead to an unnecessary drop in space-time yield of the catalyst. For the GHSV and for the pressure, the same ranges given for the first reaction zone apply. The composition of the reaction gas on entering the second stage depends on the conditions in the first stage. Accordingly, the GBL concentration is preferably from 0.2 to 2.0% by volume. The product mixture can be separated by methods known to those skilled in the art; the excess hydrogen can be circulated and reused for the hydrogenation.

In one variant of the invention, both reaction zones are accommodated in one reactor. Suitable reactors are tube reactors, shell-and-tube reactors or combinations of these. One or more heating circuits can be used to set the preferred temperatures in the two reaction zones. The hydrogenation of MA, maleic acid or its esters to form GBL and THF is associated with liberation of a large quantity of heat. The reaction enthalpy of the reaction to form GBL is higher than that of the hydrogenation of GBL to THF. In a reactor which is not operated isothermally, the temperature in the front part of the reactor will therefore be higher than in the later part. Particular preference is therefore given to generating a temperature profile along the longitudinal axis of the reactor by means of measures known to those skilled in the art so that the preferred temperatures are set in the two reaction zones of the reactor. The shape of the temperature profile depends on parameters known to those skilled in the art, for example the volume-based catalyst activity, the reaction conditions (pressure, GHSV and inlet concentration of the starting materials) and the geometry and thermostating of the reactor.

The process of the present invention makes it possible to achieve (GBL+THF) space yields of ≧98%. The GBL/THF ratio can be varied in a range of from about 90:10 to 0:100.

EXAMPLE

For the first reaction zone, 100 ml of a catalyst composed of 70% by weight of CuO, 25% by weight of ZnO and 5% by weight of $Al_2O_3$ were mixed with 100 ml of glass rings of the same size and placed in a tube reactor. The reactor was heated and the reaction gas flowed through it from the top downward. MA was pumped as a melt into a vaporizer operated at 200° C. where it was vaporized in a stream of hydrogen. The MA/hydrogen mixture having an MA concentration of 1.0% by volume was then passed through the reactor. To preheat the gas to the reaction temperature, a bed of 100 ml of glass rings was introduced above the catalyst bed.

Before feeding in the MA/hydrogen mixture, the catalyst was subjected to pretreatment with hydrogen. For this purpose, the reactor was firstly flushed with 200 standard l/h of nitrogen at atmospheric pressure and at the same time heated over a period of one hour to a temperature in the catalyst bed of 180° C. The volume flow of nitrogen was then increased to 950 standard l/h and an additional 50 standard l/h of hydrogen was fed in. A slight temperature increase in the catalyst bed to about 250° C. was observed as a result. After the temperature in the overall catalyst bed had cooled to 190° C., the volume flow of nitrogen was gradually reduced to 500 standard l/h and the hydrogen flow was increased to 500 standard l/h. Finally, the nitrogen flow was switched off and the hydrogen flow was increased to 600 standard l/h.

The reaction was carried out at 5 bar and 240° C. The GHSV was 3000 $h^{-1}$.

At complete MA conversion, no SA was detected in the gas leaving the reactor. The selectivities to GBL and THF were 88 and 10%, respectively. Overhydrogenation products (mainly butanol and butane) were formed with a selectivity of 2%.

The gases leaving the reactor were then passed to the second reaction zone. This was produced by mixing 100 ml of a catalyst composed of 40% by weight of CuO, 40% by weight of ZnO and 20% by weight of $Al_2O_3$ with 100 ml of glass rings of the same size and placing this mixture in a tube reactor. Before carrying out the reaction, the catalyst was activated by means of the above-described pretreatment with hydrogen. The reaction gases from the first stage were mixed with a stream of hydrogen in a vaporizer operated at 150° C. to adjust the temperature before feeding the gases into the second reaction zone. The GBL/THF/hydrogen gas mixture having a composition of 1.0% by volume of GBL and 0.1% by volume of THF was then passed through the reactor. The reaction was carried out at 190° C. and 5 bar. The GHSV was 3000 $h^{-1}$.

All the GBL present in the reaction gas from the first reaction zone was reacted completely. The yield of THF based on the GBL fed in was >99%. No by-product formation was observed.

The GBL conversion can be reduced by lowering the temperature, as a result of which the reaction gas contains more GBL and less THF. In the extreme case, the temperature can be reduced so far that no conversion of GBL occurs.

We claim:

1. A process for the gas-phase hydrogenation of $C_4$-dicarboxylic acids or their derivatives over a catalyst based on copper oxide to give substituted or unsubstituted γ-butyrolactone and/or tetrahydrofuran, which comprises a first reaction zone in which the $C_4$-dicarboxylic acid and/or its derivatives is/are reacted to give a mixture comprising a substituted or unsubstituted γ-butyrolactone as main product and a subsequent second reaction zone in which the substituted or unsubstituted γ-butyrolactone present in the mixture from the first hydrogenation step is reacted at a temperature lower than the temperature in the first hydrogenation step to give substituted or unsubstituted tetrahydrofuran.

2. A process as claimed in claim 1, wherein the catalyst comprises from 5 to 100% by weight of copper oxide and from 0 to 95% by weight of one or more metals or their compounds selected from the group consisting of Al, Si, Zn, La, Ce, the elements of groups IIIA to VIIIA and groups IA and IIA as active composition.

3. A process as claimed in claim 1, wherein the reaction in the first zone is carried out at ≧200° C. and the reaction in the second zone is carried out at ≦280° C.

4. A process as claimed in claim 3, wherein the reaction in the first zone is carried out at from 230 to 300° C. and the reaction in the second zone is carried out at from 150 to 240° C.

5. A process as claimed in claim 1, wherein the catalysts used in the two reaction zones have the same composition.

6. A process as claimed in claim 1, wherein the catalysts used in the two reaction zones have different compositions.

7. A process as claimed in claim 1, wherein the catalyst used in the first reaction zone comprises from 5 to 100% by weight of CuO, from 0 to 80% by weight of ZnO and from 0 to 95% by weight of $Al_2O_3$ and the catalyst used in the second reaction zone comprises from 5 to 80% by weight of CuO, from 0 to 80% by weight of ZnO and from 0 to 60% by weight of $Al_2O_3$.

8. A process as claimed in claim 7, wherein the catalyst in the first reaction zone comprises from 20 to 80% by weight of CuO, from 10 to 40% by weight of ZnO and from 5 to 60% by weight of $Al_2O_3$, and the catalyst in the second reaction zone comprises from 20 to 60% by weight of CuO, from 0 to 60% by weight of ZnO and from 10 to 50% by weight of $Al_2O_3$.

9. A process as claimed in claim 1, wherein both reaction zones are accommodated in a reactor which is not operated isothermally and in which the temperatures are set so that the temperature in the first reaction zone is higher than that in the second reaction zone.

10. A process as claimed in claim 1, wherein the pressures set in the two reaction zones are, independently of one another, from 0.5 to 100 bar.

11. A process as claimed in claim 10, wherein the pressures are from 1 to 50 bar.

12. A process as claimed in claim 10, wherein the pressures are from <20 bar.

13. A process as claimed in claim 1, wherein maleic anhydride is used as starting material.

14. A process as claimed in claim 13, wherein the maleic anhydride concentration in the first reaction step is from 0.1 to 5% by volume.

15. A process as claimed in claim 14, wherein the concentration is from 0.2 to 3% by volume.

16. A hydrogenation process as claimed in claim 1, wherein the first and second reactions are carried out, independently of one another, in a tube reactor, a shell-and-tube reactor or a fluidized-bed reactor.

17. A process as claimed in claim 1, wherein the catalyst comprises from 5 to 100% by weight of copper oxide and from 0 to 95% by weight of one or more metals or their oxides selected from the group consisting of Al, Si, Zn, La, Ce, the elements of groups IIIA to VIIIA and groups IA and IIA as active composition.

18. A process as claimed in claim 1, wherein the reaction in the first zone is carried out at from 230 to 300° C., and the reaction in the second zone is carried out at from 150 240° C.

* * * * *